United States Patent [19]

Ting

[11] 4,031,908

[45] June 28, 1977

[54] DENTAL APPLIANCE

[76] Inventor: Wen C. Ting, 31815 Maine, Livonia, Mich. 48150

[22] Filed: Sept. 4, 1975

[21] Appl. No.: 610,270

[52] U.S. Cl. .............................................. 132/91
[51] Int. Cl.² ..................................... A61C 15/00
[58] Field of Search ............... 128/62 A; 132/92 R, 132/90, 91; 32/60

[56] References Cited

UNITED STATES PATENTS

| | | | |
|---|---|---|---|
| 3,472,247 | 10/1969 | Borsum et al. | 132/91 |
| 3,481,678 | 12/1969 | Schwartzman | 401/206 |
| 3,593,707 | 7/1971 | Pifer | 128/62 A |

*Primary Examiner*—Robert Peshock
*Attorney, Agent, or Firm*—Charles W. Chandler

[57] ABSTRACT

A dental appliance having means for cleaning teeth, and means for discharging a jet of water closely adjacent the cleaning means to rinse teeth being treated by the cleaning means. In the preferred embodiment of the invention, the cleaning means comprises dental floss for cleaning between teeth. In another embodiment, the cleaning means comprises tooth brush bristles for cleaning the surface of the teeth.

3 Claims, 5 Drawing Figures

DENTAL APPLIANCE

BACKGROUND OF THE INVENTION

This invention relates to dental appliances for cleaning teeth and more particularly to means for discharging a stream of water under pressure closely adjacent a length of dental floss so as to rinse the teeth being cleaned by the floss.

A variety of dental floss holders are commercially available for removing particles from between the teeth of the user. However, such floss holders must be periodically removed from the mouth so that the user can rinse the particles from his mouth.

SUMMARY OF THE INVENTION

The broad purpose of the present invention is to provide a dental floss holder having means for connecting the holder to a source of water under pressure so that a stream of water is discharged for rinsing the teeth as the floss is being manipulated by the user to clean the teeth.

In the preffered embodiments of the invention, the appliance has an elongated body forming a handle for the user. A conduit extends through the center of the body for passing water. On end of the conduit is connected to a source of water under pressure which can be any of a variety of commercially available water jet producing devices of a conventional water faucet. The opposite end of the body has a head having a pair of arms for supporting a piece of floss between them. The floss is normally stored within the body around the conduit which delivers the water from the inlet end of the body toward an outlet opening disposed in one of the arms. The outlet opening is such that when connected to a source of pressurized water, a stream of water is delivered between the arms adjacent the position of the floss so that the user can rinse his teeth as he is cleaning them with the floss.

In another embodiment, the body supports a set of tooth brush bristles rather than a bifurcated head. In this embodiment, a stream of water is delivered into the mouth of the user from a position between the bristles so that the user can rinse his teeth as he is brushing them.

These and other objects of the invention will become readily apparent to those skilled in the art to which the invention pertains upon reference to the following detailed description.

DESCRIPTION OF THE DRAWING

The description refers to the accompanying drawing, in which like reference characters refer to like parts throughout the several views, and in which.

DESCRIPTION OF THE PREFERRED EMBODIMENTS

Figure 1:
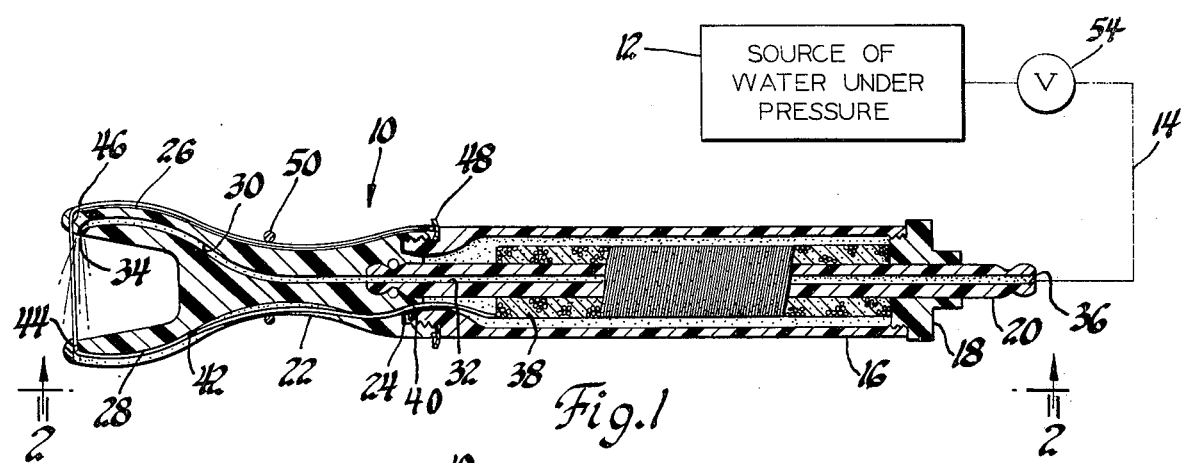
FIG. 1 is a sectional view of a dental appliance illustrating the preferred embodiment of the invention in which a source of pressurized water is illustrated schematically.

Referring to the drawing, FIG. 1 illustrates a preferred dental appliance 10 connected to a source of water under pressure 12 by conduit means 14. Source 12 may comprise any of the variety of commercially available devices for pumping water under pressure to a mouth cleaning device or a conventional water faucet. Appliance 10 comprises an elongated tubular body 16 having a plug 18 at one end supporting a tube 20. Tube 20 extends beyond plug 18 and is adapted to be connected to conduit means 14. Tube 20 is longer than body 16 so that the opposite end of the tube extends beyond the opposite end of body 16.

A head 22 is threadably mounted on body 16 at 24. Head 22 has a pair of spaced arms 26 and 28 and an internal conduit 30. One end of conduit 30 registers with a conduit 32 in tube 20 and the other end of conduit 30 is connected to an outlet opening 34 adjacent the free end of arm 26. Conduits 30 and 32 cooperate in delivering water being received through an inlet opening 36 at the opposite end of tube 20.

Figure 2:
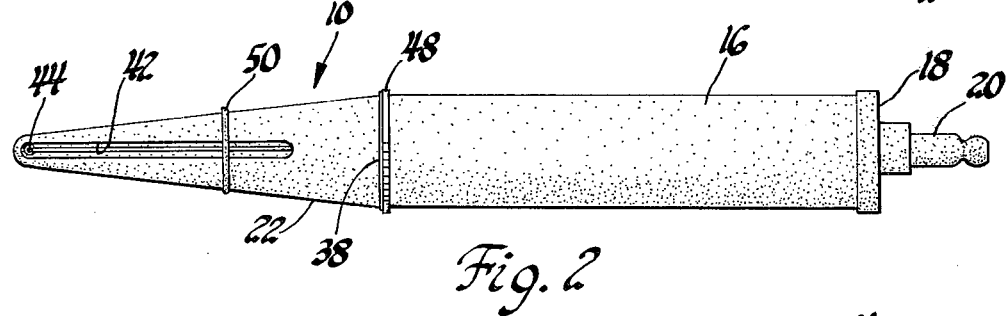
FIG. 2 is a view of the appliance of FIG. 1 taken along lines 2—2 of FIG. 1.

Referring to FIGS. 1 and 2, a quantity of dental floss 38 is stored within body 16 wrapped around tube 20. One end of floss 38 is clamped between body 16 and head 22 at 40 where the body and the head have mating conical surfaces. The floss extends from clamped position 40 along a grovve 42 in arm 28 to an opening 44. The floss extends from arm 28 toward arm 26 through an opening 46 and then back down toward the joint between the body and the head and is preferrably wrapped around the joint adjacent a tie ring 48 in such a manner that as the user screws the head onto the body, it tightly retains the end of the floss in such a manner that the floss extending between arms 28 and 26 is in a taut position.

A band 50 is disposed around head 22 to hold the floss closely adjacent the head.

A ring-shaped seal 53 is mounted between tube 20 and head 22 to prevent water leakage between these members.

In operation, the user loosens head 22 from body 16 to withdraw a sufficient length of floss from its stored position within the body. The floss is disposed to span arms 26 and 28 and then is connected adjacent tie ring 48 so that the taut floss is suited for cleaning the teeth of the user in a manner well known to those skilled in the art.

The user then manipulates a valve 54 to deliver water under pressure through inlet opening 36 toward outlet opening 34 so that the stream of water passing through outlet 34 is directed toward the center of the floss supported between the arms so that the user can rinse his teeth as he is cleaning them.

Figure 3:
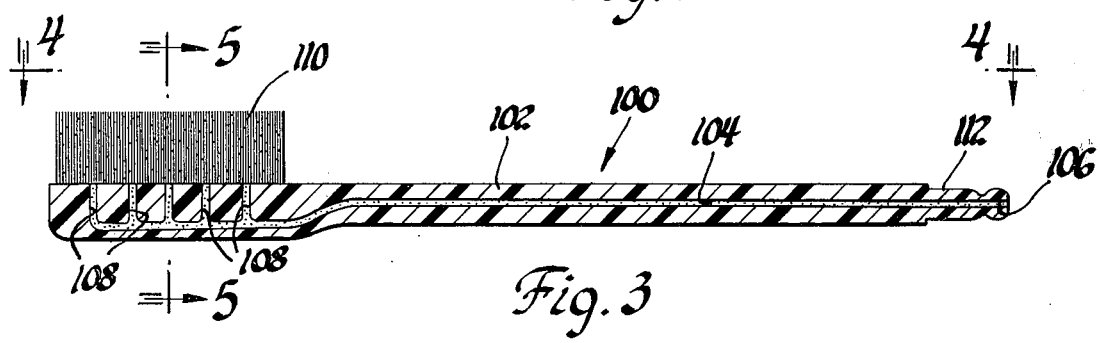
FIG. 3 is another embodiment of the invention employing tooth brush bristles.
Figure 4:
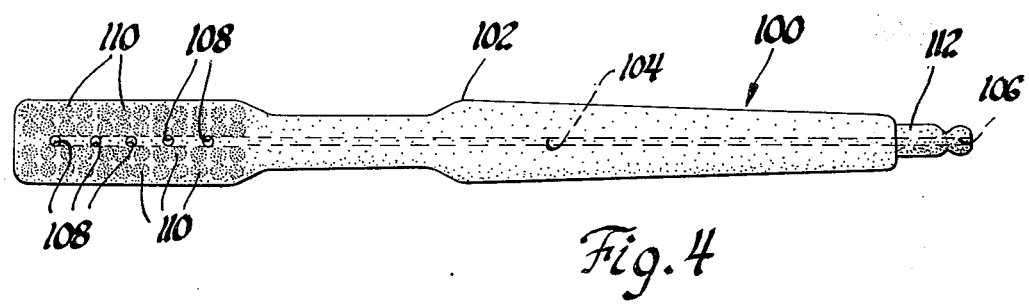
FIG. 4 is a view of the appliance of FIG. 3 taken along lines 4—4 of FIG. 3.
Figure 5:
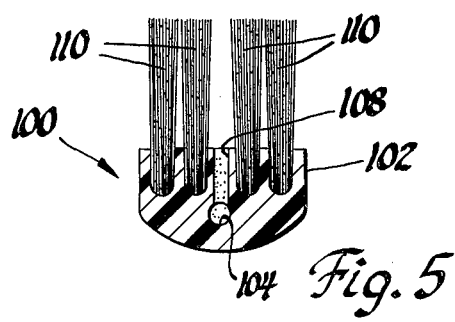
FIG. 5 is an enlarged view taken along lines 5—5 of FIG. 4.

FIGS. 3 and 4 illustrate another embodiment of the invention in the form of appliance 100. Applicance 100 comprises an elongated body 102 which is of a length sufficient to form a handle for the user to manipulate the end of the appliance within his mouth.

Appliance 100 has a longitudinal conduit 104 from an inlet opening 106 adjacent one end of the body, and a plurality of outlet openings 108 adjacent the other end of the body. A plurality of bristles 110 are supported in a position at right angles to body 102 adjacent outlet opening 108. Preferrably outlet opening 108 is adapted to discharge a stream of water parallel to bristles 110 so that the user can rinse his teeth as he is brushing them. It is to be noted that 102 has a continuous non-perforated wall extending from inlet opening 106 toward outlet opening 108 so that no foreign matter can be introduced into the water being delivered to the outlet openings. The end of body 102 is shaped at 112 so that it can be readily connected to conduit 14 of FIG. 1 for receiving water under pressure from a conventional water jet device 12.

Having described my invention, I claim:

1. Mouth cleaning apparatus comrprising:
    a source of liquid under pressure;
    a hollow body;
    a head mounted on the body, said head having a pair of spaced arms suited for supporting a length of dental floss between them, a first of said arms having an opening, and first conduit means connected with said opening for discharging a stream of liquid adjacent said arms;
    an elongated tube having one end connected to the head so as to be supported in the body, the tube being connected to the source of liquid under pressure and having longitudinal second conduit means fluidly connected to the first conduit means for cooperating therewith for passing liquid therethrough from said source to the opening in the head;
    plug means mounted on the body opposite the head for supporting the tube end opposite the end connected to the head, the plug being removeable from the body to permit removal of the tube therefrom, and to permit access into the body; and
    a length of dental floss disposed in the body in a stored position about the tube and the second conduit means, the floss being extended from said stored position in the body so as to be connected between the arms of the head in a position adjacent said head opening, the floss on one side of the arm being clamped betweem the head and the body and the floss on the opposite side of the arms being connected to the head whereby the floss between the arms is supported in a taut position for removing matter from the teeth of the user as a stream of liquid is being discharged adjacent the floss.

2. Apparatus as defined in claim 1, in which the opening is disposed in said first arm to discharge liquid toward the opposite arm of said pair.

3. Apparatus as defined in claim 1, in which the body means form a handle for the user to manipulate the pair or arms.

* * * * *